US006432676B1

(12) United States Patent
Tubert et al.

(10) Patent No.: US 6,432,676 B1
(45) Date of Patent: *Aug. 13, 2002

(54) CHIMERIC GENE USING THE GENE OR CDNA OF INSULIN, SPECIALLY FOR THE GENE THERAPY OF DIABETES

(75) Inventors: Fatima Bosch Tubert; Alfons Valera Abril, both of Cerdanyola (ES)

(73) Assignee: Universitat Autonoma de Barcelona, Bellaterra (ES)

(*) Notice: Subject to any disclaimer, the term of this patent is extended or adjusted under 35 U.S.C. 154(b) by 0 days.

This patent is subject to a terminal disclaimer.

(21) Appl. No.: 09/565,728

(22) Filed: May 5, 2000

Related U.S. Application Data

(63) Continuation of application No. 08/553,576, filed as application No. PCT/ES94/00027 on Mar. 14, 1994, now Pat. No. 6,137,029.

(51) Int. Cl.[7] ........................... C12P 21/06; C12P 21/04; C12N 15/00; C12N 5/00; C12N 15/63
(52) U.S. Cl. .................. 435/69.4; 435/70.1; 435/320.1; 435/325; 435/455
(58) Field of Search ...................... 435/325; 424/93.21; 514/44; 800/3, 8, 9, 11, 13, 18

(56) References Cited

U.S. PATENT DOCUMENTS 6,137,029 A * 10/2000 Tubert et al. ................. 800/18

OTHER PUBLICATIONS

Ledley; Clinical Considerations in the Design of Protocols for Somatic Gene Therapy, 1991, Human Gene Therapy 2:77–83.*
Eck et al.; Gene–Based Therapy, 1996, Pharmacological Basis of Therapeutics, Chapter 5: 77–101.*
Miller et al.; Targeted vectors for gene therapy, 1995, FASEB J. 9: 190–199.*
Deonarain; Ligand–targeted receptor–mediated vectors for gene delivery, 1998, Exp. Opin. Ther. Patents 8(1): 53–69.*
Verma et al.; Gene therapy– promises, problems and prospects, 1997, Nature, vol. 389: 239–242.*
Crystal; Transfer of Genes to Human: Early Lessons and Obstacles to Success, 1995, Science vol. 270: 404–410.*
Docherty; Gene therapy for diabetes mellitus, 1997, Clinical Science 92: 321–330.*
Freeman et al.; Present and potential future use of gene therapy for the treatment of non–insulin dependent diabetes mellitus(Review); 1999, International Journal of Molecular Medicine4: 585–592.*
Vollenweider, et al., "Processing of Proinsulin by Transfected Hepatoma (FAO) Cells", The Journal of Biological Chemistry, vol. 267, No. 21, Issue of Jul. 25, pp. 14629–14636, 1992.
Simpson, et al., "Functional expression of human insulin gene in a human hepatoma cell line (HEP G2)", Gene Therapy (1995), vol. 2, No. 3, May 1995, pp. 223–231.
Kolodka, et al., "Gene therapy for diabetes mellitus in rats by hepatic expression of insulin", Proc. Natl. Acad. Sci. USA, vol. 92, Apr. 1995, pp. 3293–3297.

* cited by examiner

Primary Examiner—Deborah Crouch
Assistant Examiner—Thaian N. Ton
(74) Attorney, Agent, or Firm—Steinberg & Raksin, P.C.

(57) ABSTRACT

The chimeric gene is directed by a promoter or fusion of promoters which preferably are regulable and activated by the diabetic process. Preferably, it is obtained by fusion of the human insulin gene to the promoter of PEPCK (P-enolpiruvate carboxiquinasa). Said promoter (fragment −460 bp to +73 bp) is fused to the flank zone 5' of the human insulin gene (−170 bp to +1). The gene of the human insulin contains two coding exons E1 and E2 and two introns A and B. It also relates to an expression vector which allows the expression of insulin in cells which are different from the β-cells of the pancreas, and to a transgenic animal which expresses said chimeric gene. It is especially used for the gene therapy of diabetes.

9 Claims, 3 Drawing Sheets

CHIMERIC GENE USING THE GENE OR CDNA OF INSULIN, SPECIALLY FOR THE GENE THERAPY OF DIABETES

This application is a continuation of Ser. No. 08/553,576 filed Jun. 3, 1996 copending U.S. Pat. No. 6,137,029, filed on Jun. 3, 1996, which in turn claims priority from PCT/ES94/00027, filed on Mar. 14, 1994, the disclosures of which are incorporated by reference herein in their entireties.

The present invention relates firstly to a chimeric gene using the gene or CDNA (complementary DNA) of insulin driven by a promoter or fusion of promoters.

More specifically, it relates to the design of a chimeric gene formed by the fusion of the promoter of P-enolpyruvate carboxyquinase to the structural gene of human insulin, which allows the production of human insulin, physiologically regulated, in a tissue different from the pancreas.

The invention further relates to others objects which are described below.

BACKGROUND OF THE INVENTION

Patients suffering from insulin dependent diabetes mellitus (IDDM) (type I) depend dramatically on the administration of the hormone. The interruption of the insulin administration results first in hyperglycemia and ketoacidosis, then coma and finally death if the hormone is not injected. Therefore, the life and the quality of life of these patients depend completely on the fluctuations of the insulin levels in their blood.

Gene therapy consists in the transfer of genetic material into cells of a patient with the purpose of treating an illness. At present, different approximations of gene therapy are being developed, based on the introduction of genes directly into animals or cells which are then transplanted.

However, the most important goal is not to be able to transplant successfully cells expressing the gene in an animal, but to make it possible for the gene to express in a regulated and physiologic way. The choice of a good promoter which drives the expression of the suitable gene is crucial in order to obtain suitable plasmatic levels of the corresponding protein.

In the case of diabetes, the question is to chose the promoter which drives the expression of the gene in order to obtain suitable insulin plasmatic levels for every condition of the individual. The overexpression of the insulin gene would result in hypoglucemia and a low expression of said gene would not modify the high glucose levels in the diabetic process.

BRIEF DESCRIPTION OF THE DRAWINGS

In order to better understand the disclosure herein, the following drawings of exemplary embodiments are provided.

In the drawings.

DESCRIPTION OF THE INVENTION

Figure 1:
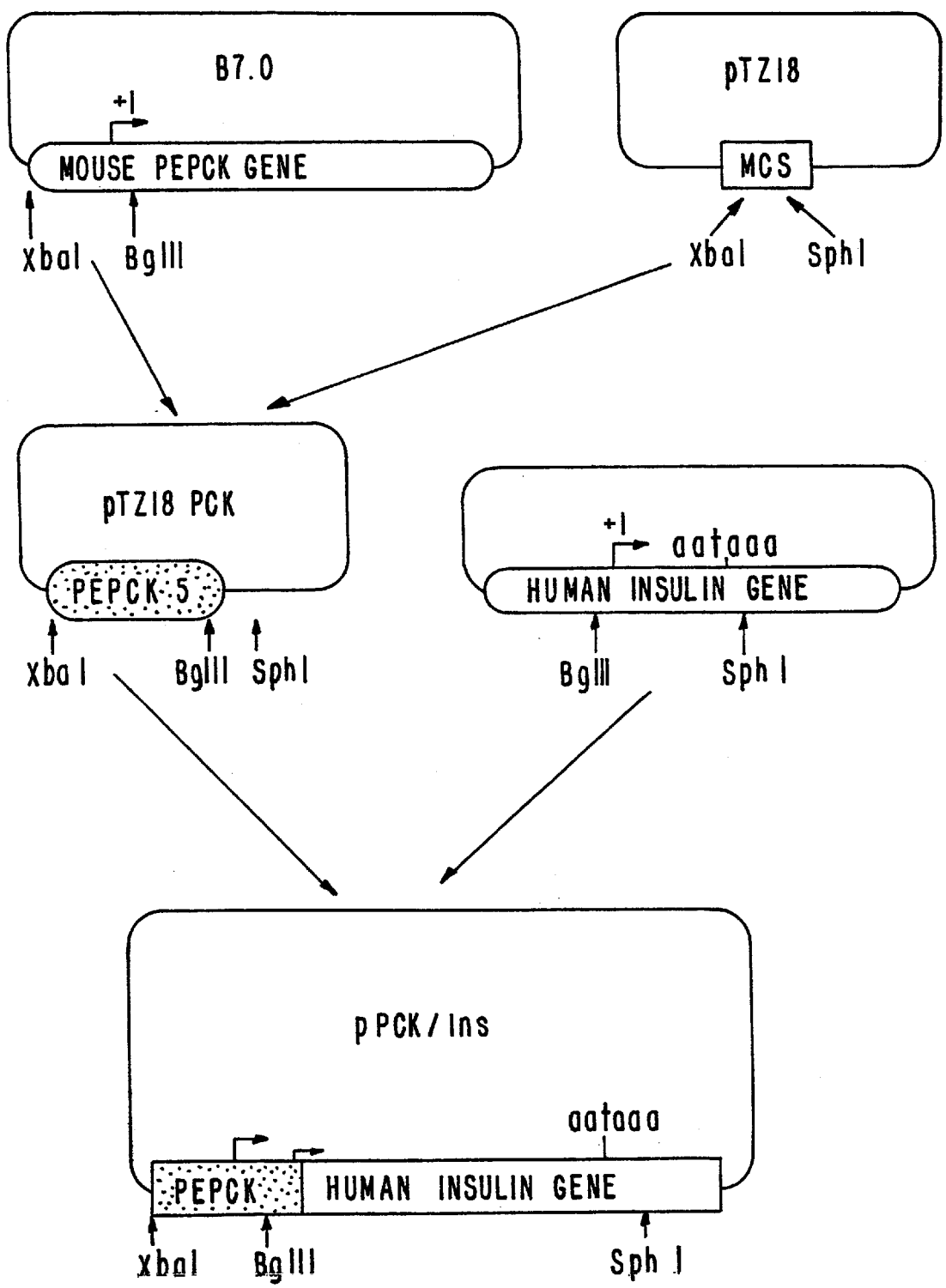
FIG. 1 shows the construction of the PEPCK/insulin chimeric gene from the plasmid pB7.0 and the human insulin gene.

One object of the invention is a chimeric gene using the gene or cDNA (complementary DNA) of insulin driven by a promoter or fusion of promoters, preferably adjustable and activated by the diabetic process.

Preferably, the object of the invention is a chimeric gene which is obtained by fusion of the human insulin gene to the promoter of the P-enolpyruvate carboxyquinase (PEPCK).

P-enolpyruvate carboxyquinase is a key enzyme for the control of the gluconeogenic via, and it is found mainly in the liver, kidney, jejunum and adipose tissue. The activity of this enzyme is regulated as regards the expression of its gene. (Hanson, R. W., et al. (1976) Gluconeogenesis: Its Regulation in mammalian Species. John Wiley & Sons, Inc., New York). The expression of the gene of PEPCK is finely regulated by hormones. Within the fragment of the promoter of PEPCK used (−550 bp to +73 bp) sequences responding to AMPc, glucocorticoids and insulin have been described (Wynshaw-Boris, A. et al. (1984) J. Biol. Chem. 259, 12161–12169; Wynshaw-Boris, A., et al. (1986) J. Chem. 261, 9714–9720; Short, J. M., et al. (1986) J. Biol. Chem. 261, 9721–9726; O'Brien, R. M., et al. (1990) Science 249, 533–537). The glucagon, acting via AMPc, and the glucocorticoids activate the gene expression, while insulin inhibits said expression. The gene expression of the PEPCK is increased in diabetic animals due to the rise in the plasmatic levels of glucagon and the drop in the insulin levels (Tilghman, S. M., et al. (1974) Proc. Natl. Acad. Sci. USA 71, 1304–1308; Hopgood, M. F., et al (1973) Biochem. J. 134, 445–453; Kioussis, D., et al. (1978) J. Biol. Chem. 253, 4327–4332). This fragment of the promoter of PEPCK is able to drive the gene expression of the bovine growth hormone, in a regulated and specific way, of tissue in transgenic animals (NcGrane, MlM., et al.(1988) J. Biol. Chem. 263, 11443–11451; Short, M. K., et al. (1992) Mol. Cell. Biol. 12, 1007–1020; Eisenberger, C. L. (1992) Mol. Cell. Biol. 12, 1396–1403).

Therefore, when fused to the human insulin gene, this promoter of PEPCK insulin will be produced in the tissues where the promoter of PEPCK is expressed. In a diabetic animal the chimeric gene will be transcribed, but when sufficient insulin is synthesized, the insulin itself will inhibit the promoter of PEPCK which drives its expression.

So the object of the invention is the creation of a PEPCK/insulin chimeric gene. In this chimeric gene, the fragment corresponding to the insulin gene keeps 170 bp of the flank zone 5'. The PEPCK/insulin chimeric gene contains two beginnings of transcription, one corresponding to the insulin promoter, and the other one the promoter of PEPCK.

It is actually a chimeric promoter, to which the portion of the promoter of PEPCK confers tissue specificity (mainly liver, kidney, jejunum and adipose). This chimeric gene has been introduced into hepatoma cells in culture and into hepatocytes in primary culture by transitory transfection, the appearance in these cells of insulin specific mRNA in liver and immunoreactive insulin in the culture medium-being observed.

Another object of the invention is a method for fusioning promoters or gene regulating elements which allows to express insulin in cell types different from the β-cells of the pancreas. In the chimeric gene, the portion of the promoter of PEPCK confers tissue specificity (mainly liver, kidney, jejunum and adipose).

Also an object of the invention is an expression vector which allows to express insulin in cells different from the β-cells of the pancreas, more particularly, a pPCK/Ins plasmid vector and a vPCK/Ins retroviral vector. These vectors allow the expression of the chimeric gene in cells. Other vectors of viral expression (adenovirus, herpes, virus, papillomavirus, etc.) or non-viral can be used.

They have been used to infect different types of cells in primary culture and established cell lines (hepatoma, fibroblasts, myoblasts, preadipocytes). The infected cell lines express human insulin in a predictable way.

Further, the object of the invention is a transgenic animal expressing the chimeric gene described above, as well as a cell type originated from this transgenic animal.

Transgenic mice have been obtained in the laboratory by means of the technique of microinjection of the chimeric gene into fertilized mouse eggs before the fusion of both the female and male pronuclei. The animals obtained were healthy and normoglycemic, showing that there is a good control in the regulation of the chimeric gene.

Another object of the invention is the chromosome of the transgenic animal containing the above described chimeric gene.

Finally, the object of the invention is a chimeric gene of the above described type, for using in the gene therapy of diabetes, more specifically, for using in the gene therapy of diabetes in tissues different from the pancreas in mammals, particularly, in the human species.

Also, the invention relates to a transgenic animal of the type disclosed for using in the development of gene therapy protocols.

For the construction of the PEPCK/insulin chimeric gene (FIG. 1) we started from plasmid pB7.0 which contains the complete gene of PEPCK. By means of digestion with the XbaI and BglII enzymes (fragment from −460 bp to +73 bp), the flank zone 5' of this gene was obtained. This fragment was then subcloned in the polylinker of the pTZ18 plasmid. To this end, this plasmid was driven with XbaI and BGlII and the fragment of the promoter was later linked to these target sites. The promoter of PEPCK had been subcloned in pTZ18 and there were still some targets in the polylinker that could later be used. Then the human insulin gene was introduced. In this case, the complete gene of insulin was cut with BGlII and SphI and the fragment −170 bp to +1561 bp was obtained (Bell, I. B., et al (1980) Nature 284, 26–32). The pTZ18 plasmid, which contained the promoter of PEPCK, was driven with BglII a target situated at the end of the promoter (end 3'), and SphI, a target situated on the polylinker. This linearized plasmid was linked to the fragment BglII/SphI of the insulin gene, and the PEPCK/insulin chimeric gene was obtained, subcloned in pTZ18 (FIG. 1). This plasmid was named pPCK/Ins.

Figure 2:
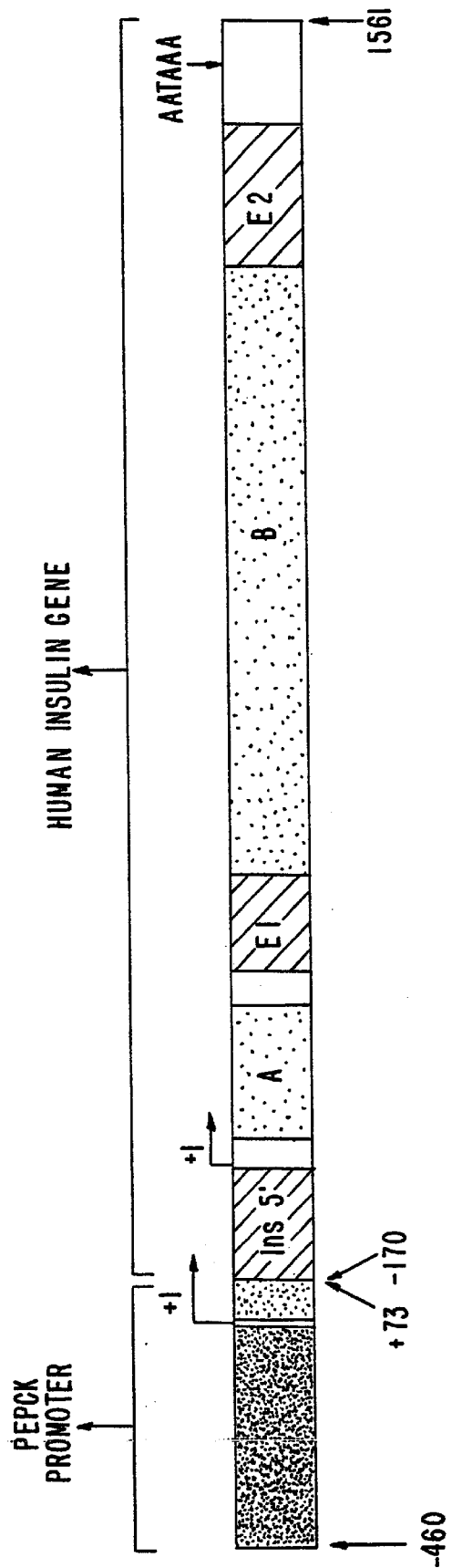
FIG. 2 shows the structure of the PEPCK/insulin chimeric gene.

FIG. 2 shows, in detail, the structure of the PEPCK/insulin chimeric gene. The promoter of PEPCK (fragment −460 bp to +73 bp) is fusioned to flank zone 5' of the human insulin gene (−170 bp to +1). This fragment of the promoter of insulin contains the elements recognized by the general machinery of transcription and a *response element to AMPc (which induces the expression of the gene). Therefore, in the flank zone 5' of the chimeric gene were two TATA box and two beginnings of the transcription, one at the end of the promoter of PEPCK and another one at the end of the promoter of insulin. The human insulin gene contains three exons (two codifiers, E1 and E2) and two introns (A and B). In position 5' with respect to the intron A is the cap site and in 3' of the last exon is the polyadenylation signal (FIG. 2).

This chimeric gene has been introduced in hepatoma cells in culture and in hepatocytes in primary culture by transient transfection with the pPCK/Ins plasmid Insulin specific mRNA was observed in these cells, and immunoreactive insulin was observed in the culture medium.

Once it was verified that the PEPCK/insulin chimeric gene was expressed in a predictable way, we prepared a retroviral vector containing the chimeric gene. The chimeric gene is expressed in a way regulated and controllable by the expression product itself, insulin. This is an essential requirement for producing a vector useful in gene therapy.

Figure 3:
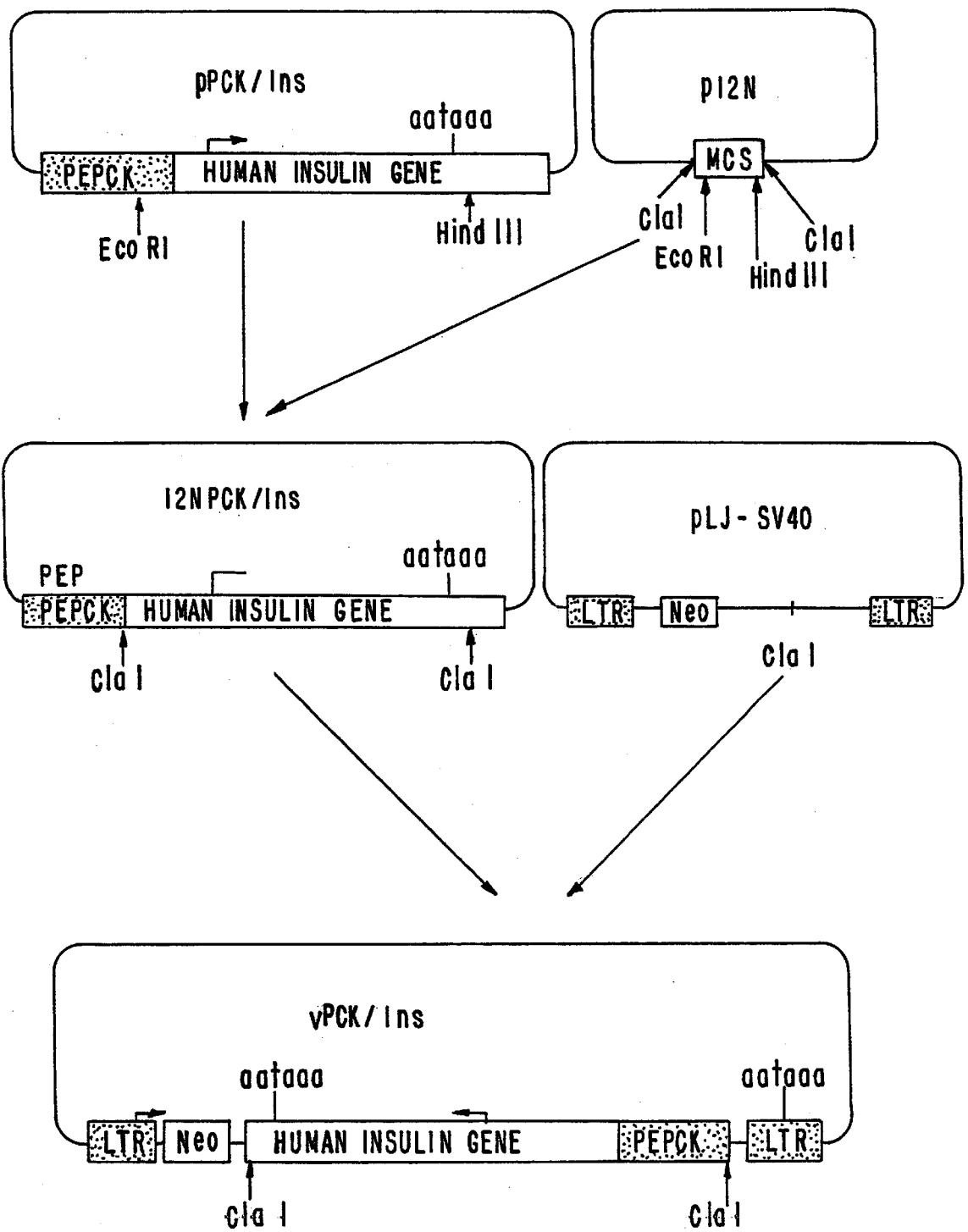
FIG. 3 shows the process for obtaining the vPCK/Ins retroviral vector from the pPCK/Ins plasmid.

As schematically shown in FIG. 3, the fragment EcoRI-HindIII of the pPCK/Ins plasmid was subcloned for the construction of the retroviral vector, said fragment containing the complete PEPCK/insulin chimeric gene, to the plasmid p12N. The Cla I fragment of the p12NPCK/Ins was then obtained, containing the chimeric gene, and introduced in the Cla I target of the pLJ(-SV40) retroviral vector (derivative from the pLJ parental vector (Korman, A. J., et al. (1987) Proc. Natl. Acad. Sci. USA 84, 2150–2154)). The resulting vector, vPCK/Ins, contains the PEPCK/insulin chimeric gene in an orientation opposite to the LTR 5' (promoter of the retrovirus).

This vector was introduced in psi-2 cells (Mann, R., (1983) Cell 33, 153–159) by precipitation with calcium phosphate. The cells were exposed to the selection antibiotic G418 at 48 hours after transfection, and those which were positive to the integration of the vector survived the toxic. These cells were kept in culture for a month, and when they reached confluence the culture medium was collected, which contained the defective virions.

The process for obtaining a transgenic animal expressing the PEPCK/insulin chimeric gene is briefly described below.

Once verified that the chimeric gene was functional by transfection of culture cells, the chimeric gene was then microinjected (XbaI-SphI fragmento) to mouse fertilized ovules before the fusion of both the female and male pronuclei according to the method described in Wagner,. et al. (1981) Proc. Natl. Acad. Sci. USA 78, 5016. These embryos were then transferred to a receptor mother. DNA of the obtained animals was isolated from a tail fragment and then the presence of the transgene was analyzed by Southern blot and further hybridization with a specific probe containing a fragment of the microinjected chimeric gene. With the transgenic animals colonies have been established, in which the expression of the chimeric gene has been analyzed. So the transgenic animals obtained express the transgene in those tissues where PEPCK is ussually expressed. The obtained animals were healthy and normoglycemic, thus showing that there is a good control in the regulation of the chimeric gene.

What is claimed is:

1. A method for producing human insulin comprising:

transforming mammalian cells with a gene construct to produce transformed mammalian cells;

wherein said gene construct comprises a PEPCK promoter in operable linkage with a human insulin gene; and growing said transformed mammalian cells under conditions favorable for expression of said gene construct.

2. The method of claim 1, wherein said transformed mammalian cells are grown under conditions favorable for producing insulin in quantities greater than are produced by non-transformed mammalian cells grown under the same conditions.

3. The method of claim 1, wherein said gene construct is expressed in a cell or cells other than pancreatic beta cells.

4. The method of claim 1, wherein the mammalian cells are selected from the group consisting of liver, kidney, jejunum and adipose cells of a mammal.

5. The method of claim 1, wherein expression of said human insulin gene is downregulated in the presence of insulin.

6. The method of claim 1, wherein expression of said human insulin gene is upregulated in the presence of glucagon.

7. The method of claim 1 wherein said gene construct is the plasmid vector pPCK/Ins.

8. The method of claim 1 wherein said gene construct is the retroviral vector vPCK/Ins.

9. The method of claim 1 wherein said PEPCK promoter consists essentially of a PEPCK fragment ranging from −460 bp to +73 bp as defined by FIG. 2.

* * * * *